US008662082B2

(12) United States Patent
Bogojevic et al.

(10) Patent No.: US 8,662,082 B2
(45) Date of Patent: Mar. 4, 2014

(54) STERILE DRAPE

(75) Inventors: Aleksander Bogojevic, Munich (DE); Christian Maier, Munich (DE); Georg Christian, Munich (DE); Jörg Uhde, Munich (DE)

(73) Assignee: Brainlab AG, Feldkirchen (DE)

( * ) Notice: Subject to any disclaimer, the term of this patent is extended or adjusted under 35 U.S.C. 154(b) by 1045 days.

(21) Appl. No.: 11/626,527

(22) Filed: Jan. 24, 2007

(65) Prior Publication Data

US 2007/0175486 A1    Aug. 2, 2007

Related U.S. Application Data

(60) Provisional application No. 60/765,056, filed on Feb. 3, 2006.

(30) Foreign Application Priority Data

Jan. 24, 2006   (EP) ..................... 06001408

(51) Int. Cl.
*A61B 19/00*   (2006.01)
*A61B 19/02*   (2006.01)

(52) U.S. Cl.
USPC ........................... 128/849; 128/856; 150/154

(58) Field of Classification Search
USPC ......... 128/846, 849, 852, 856, 869, 872, 874, 128/876; 602/19, 60, 75, 3; 2/110, 311, 2/312, 338; 150/154, 165; 600/121, 122; 359/507, 510, 511; 378/203; 250/515.1, 216.1, 519.1

See application file for complete search history.

(56) References Cited

U.S. PATENT DOCUMENTS

| | | | | |
|---|---|---|---|---|
| 1,647,169 A | * | 11/1927 | Anton ........................... | 150/154 |
| 3,706,276 A | * | 12/1972 | Yamada et al. ................ | 101/453 |
| 4,372,303 A | * | 2/1983 | Grossmann et al. .......... | 128/851 |
| 4,614,183 A | * | 9/1986 | McCracken et al. .......... | 128/846 |
| 4,699,146 A | * | 10/1987 | Sieverding .................... | 600/391 |
| 5,183,664 A | * | 2/1993 | Ansell ........................... | 424/445 |
| 5,197,493 A | * | 3/1993 | Grier-Idris .................... | 128/853 |
| 5,490,524 A | * | 2/1996 | Williams et al. .............. | 128/849 |
| 5,592,953 A | * | 1/1997 | Delao ........................... | 128/882 |
| 5,802,719 A | | 9/1998 | O'Farrell, Jr. et al. | |
| 5,812,188 A | | 9/1998 | Adair | |
| 5,891,020 A | | 4/1999 | Luber et al. | |
| 6,000,400 A | * | 12/1999 | Navis ............................ | 128/849 |
| 6,283,125 B1 | * | 9/2001 | McNeirney et al. .......... | 128/853 |
| 6,481,888 B1 | | 11/2002 | Morgan | |
| 6,512,158 B1 | * | 1/2003 | Dobos ........................... | 602/41 |
| 6,697,664 B2 | | 2/2004 | Kienzle, III et al. | |
| 2001/0036245 A1 | | 11/2001 | Kienzle, III et al. | |
| 2003/0153810 A1 | | 8/2003 | Bertolero et al. | |

* cited by examiner

*Primary Examiner* — Patricia Bianco
*Assistant Examiner* — Keri J Nelson
(74) *Attorney, Agent, or Firm* — Tucker Ellis LLP

(57) ABSTRACT

A sterile drape for a trackable medical device includes a reinforced film portion and a holding or tensing device. The holding or tensing device is operative to draw the reinforced film portion taut or smooth on or over a surface of the medical device.

19 Claims, 1 Drawing Sheet

STERILE DRAPE

RELATED APPLICATION DATA

This application claims priority of U.S. Provisional Application No. 60/765,056 filed on Feb. 3, 2006, which is incorporated herein by reference in its entirety.

FIELD OF THE INVENTION

The invention relates to a sterile drape such as is used to cover objects in a sterile environment, for example in operating theaters. In particular, the sterile drape is suitable for tracking objects, such as attachments of C-arm x-ray apparatus.

BACKGROUND OF THE INVENTION

In order to maintain a sterile environment, C-arms and/or their tracking attachments are conventionally covered with tubular or pouch-shaped films. There are a number of drapes for C-arms that are used to sterilely cover various parts of the C-arm apparatus, including, for example, the image intensifier. These drapes generally comprise an inner side that faces the part to be covered (e.g., the C-arm or its parts, such as a cylindrical tracking attachment with reflector marker attachments) and an outer, sterile side that faces the sterile environment of the operating theater.

Conventional C-arm drapes are known, for example, from U.S. Pat. No. 6,697,664 and from U.S. Pat. No. 5,802,719. In U.S. Pat. No. 5,802,719, the drape, which may cover an inner part of the C-arm, is flexible and may be drawn into shape by a number of clips that can be attached to the frame of the C-arm. A drape for shielding x-rays from being scattered by the operating table is known from U.S. Pat. No. 6,481,888.

The known covering films may be manufactured from a relatively thin material. This may be done deliberately so as to enable the drapes to remain flexible and to be easily draped over objects. However, conventional drapes are so flexible that they often form creases and plaits (also referred to as pleats) when they are drawn over an object. Such creases and plaits can become a problem when the object to be covered is to be detected by a tracking system.

Optical tracking systems typically receive either actively emitted light (e.g., light flashes), which in most cases are in the infrared spectrum, or light passively reflected off of specialized reflector markers. Tracking attachments for the image intensifiers of C-arms, for example, may have a number of such reflector markers on their outer surface (the surface may have a cylindrical periphery). If these markers are then covered with a film that has creases and plaits and, for example, if a crease or plait is situated over a reflection marker, its reflection image can be distorted (scattered). This can result in a camera tracking system incorrectly detecting the position of the marker in three-dimensional space, which in turn can distort registration of the x-ray recordings produced using the C-arm.

SUMMARY OF THE INVENTION

An exemplary sterile drape includes a reinforced film portion, and a holding or tensing means. The holding or tensing means enables the reinforced film portion to be drawn taut or smooth on or over a surface. In other words, at least a part of the drape can be made crease-free and plait-free such that it is ensured (e.g., by the holding or tensing means) that at least this crease-free and plait-free reinforced film portion tightly fits the object to be covered. In this way, it is possible to ensure that the covered object or at least portions thereof are covered by a smooth (and in particular also taut), tight-fitting part of the film, such that objects of interest on the surface also can be recognized through the drape.

In other words, the sterile drape includes a film portion that is dimensionally stable or stable in its shape and, for example, can be used to cover a part of an object, such as a C-arm, wherein the C-arm and/or tracking elements attached to the C-arm are visible to a tracking system (e.g., a camera tracking system or the like). This "visible" part of the C-arm can include or be used to mount a registration kit (tracking attachment) that is used in image-guided surgery. The registration kit can include markers that are optically tracked by a camera tracking system, for example. Since the drape provides a clear view of the markers to the camera system, highly accurate tracking data can be obtained and provided to a navigation system, thereby enhancing accuracy.

The sterile drape (or at least its reinforced film portion) can be formed as a wrap-around or sheath for the object to be covered. The drape can be formed as a pouch-like sheath with a reinforced portion and a non-reinforced remaining portion. As a wrap-around or sheath, the drape is suitable for smooth and/or plane surfaces, e.g., for all apparatus whose surface features are to be easily visible and on which the film is to lie as a smooth sheet (e.g., a laminar surface). One example is the cylindrical outer surface of a registration kit as discussed above.

The reinforced film portion can be fabricated such that it can maintain a smooth shape. The reinforced film portion can comprise a material having the following properties:

- having greater than 1.5 times, particularly greater than 3 to 4 times, and more particularly greater than 6 to 8 times as thick as a conventional clinical sterile covering film; and/or
- having 1.5 to 15 times, particularly 4 to 12 times, and more particularly 7 to 10 times as thick as a conventional clinical sterile covering film (which can be 30 to 50 µm thick, for example).

The reinforced film portion also comprise a material having the following properties:

- having greater than 1.5 times, particularly greater than 3 to 4 times, and even more particularly greater than 6 to 8 times as thick as the remaining transparent film of the drape; and/or
- having 1.5 to 15 times, particularly 4 to 12 times, and more particularly 7 to 10 times as thick as the remaining transparent film of the drape (which can be 30 to 50 µm thick, for example).

The reinforced film portion can include different material from the remaining transparent film of the drape, in particular a material that by its material nature is more rigid and more resistant to folding.

The reinforced film portion can exhibit transparency to electromagentic radiation in certain spectrums, e.g., transparency in the infrared spectrum and/or in the visible spectrum. The reinforced film portion can be formed to have a rectangular shape and can extend from one edge of the drape to an opposite edge of the drape.

The holding or tensing means of the sterile drape can assume or otherwise be formed having many different shapes. Non-limiting examples include: a belt tie, in particular a belt-hole tie (as with laces on shoes); a rubber tie; a Velcro® fastening; a hooked tie or hooked fastening; and/or an adhesive or bonded fastening. Any combination of at least two of the above holding or tensing means or other holding or tensing means can of course also be used.

BRIEF DESCRIPTION OF THE DRAWINGS

The forgoing and other features of the invention are hereinafter discussed with reference to the drawings.

DETAILED DESCRIPTION

Figure 1:
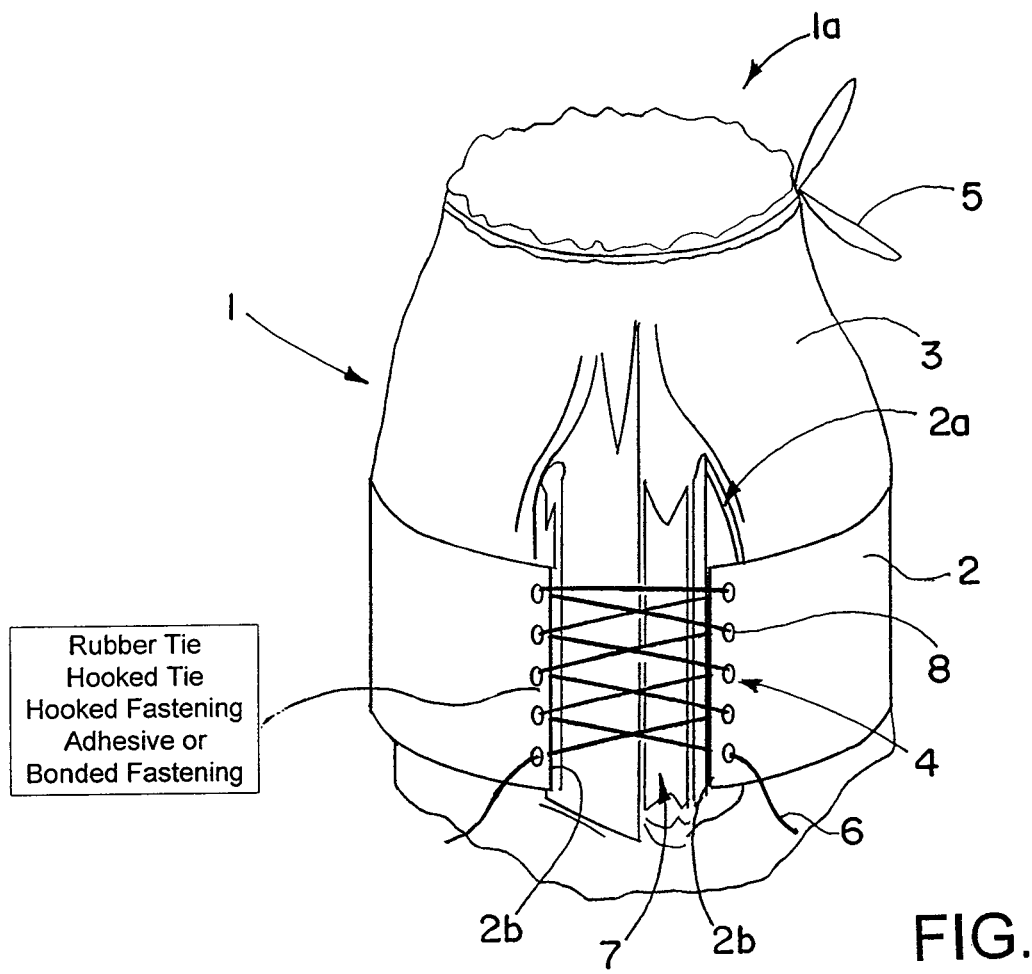
FIG. 1 illustrates an exemplary drape formed as a tubular film in accordance with the invention.

Referring to FIG. 1, an exemplary sterile drape 1 may be formed having a tubular shape. The drape 1 includes an annular, reinforced portion 2 (e.g., a reinforced film portion) and a remaining film portion 3 (e.g., a tubular portion 3, also referred to as a second portion or draping portion) made of conventional, thin film material. The film material in the reinforced portion 2 and film portion 3 can be permeable to light, for example, in the visible and/or infrared spectrum.

The film portion 3, which may be formed thinner relative to the reinforced portion 2, can include a thread tie 5 on its one side (e.g., an upper side or end). The thread tie 5 can be used to seal the drape 1 on one end 1a of the drape 1. The reinforced portion 2 can be formed as a belt 6, wherein, for example, an open end 2a of the reinforced portion 2 can include holes 8 along an edge portion 2b of the open end 2a. The belt 6 can be threaded through the holes 8 so as to form a belt tie 4. The belt tie 4 can be drawn tight or taut like the laces of a shoe and so draped over an object to be covered. An area 7 is also shown, wherein the area 7 may be drawn taut via the belt tie 4 and the film portion 3 may be drawn together and creased.

The drape 1 can be used as a C-arm drape, and can include a non-sterile inner side and a sterile outer side. The drape 1 can be "hermetically" sealed in the sense that its parts are connected to each other (for example by fused seams, bonded seams, bonded points or by liberal overlapping) in such a way that the sterility of the outer side of the drape 1 is ensured, while the inner side may be non-sterile. When covering a C-arm, the upper end of the film portion 3, which can exhibit the shape of a tube, can be slid or placed over the arm from the image-intensifier end of the C-arm. This end then has the thread tie 5, which can be used to attach the drape 1 to the C-arm and/or to close the end with the thread tie 5 around the arm, wherein bonding strips also may be used, for example.

The reinforced portion 2, which may be provided on the lower portion of the drape 1, can be transparent and exhibit a rigid flexibility. Due to its material properties and stability, the reinforced portion 2 can be bent but not folded when properly used, such that it does not crease. The reinforced portion 2 can include material that is transparent to particular wavelengths of the electromagnetic spectrum, such as the visible and/or infrared spectrum, for example. The shape of the reinforced portion can be configured in such a way that longer sides are hermetically connected to the film portion 3. The shorter sides, e.g., the edges, are (or can be) flexibly connected in such a way that they can be converged and fixed with the aid of the holding or tensing means, e.g., the belt tie 4.

The lower end 1a of the drape 1 shown in FIG. 1 can include the film portion 3, e.g., the typical and conventional covering film. The lower end 1a can be closed (pouch-like) or in turn hermetically sealable in a suitable way (laces, bonding strips). The intermediate space at the creasing point 7 can be hermetically sealed with film. This portion 7 can be an extension of the film portion 3 or also of the reinforced portion 2, and in general terms, all the parts can be embodied integrally, connected integrally to each other, produced from one piece, or provided individually and connected to each other or arranged with each other.

Figure 2:
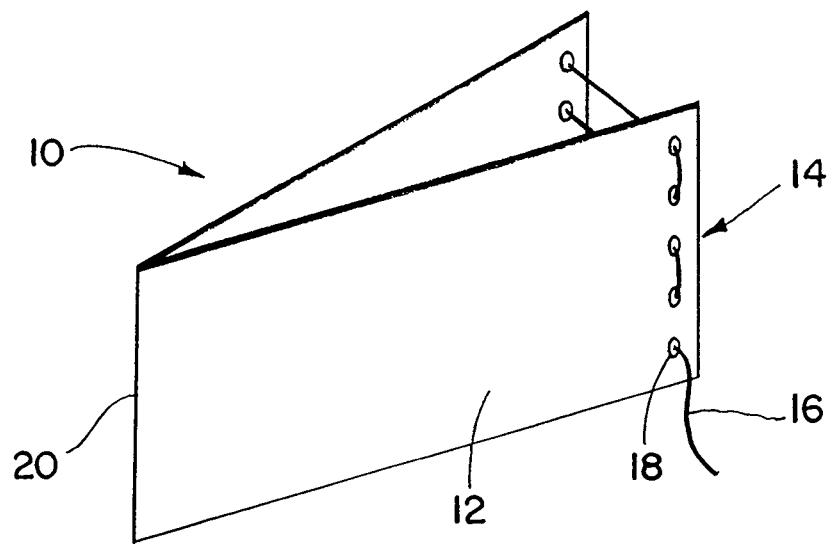
FIG. 2 illustrates an exemplary reinforced, pre-folded film portion of a drape in accordance with the invention.

FIG. 2 shows another embodiment of a reinforced portion 12 of a drape 10, i.e., only the reinforced portion 12. This portion also can include a belt tie 14 with holes 18 and a belt 16, and can include a fold 20 on an opposite side such that the reinforced portion 10 can be creased in a defined or predetermined way. Such predetermined folds or creasing points, for example, are advantageous for transport and storage, because the drape 10 is not creased for stowing or transport at points at undesirable or random points. Damage, which can impair the functionality of the drape, is avoided. A number of folds can be provided, or also "hermetic" hinge mechanisms.

The exemplary drapes 1 and 10 are particularly suited for being drawn over the outside of a cylindrical registration kit of a C-arm image intensifiers. The reinforced portion, which can be cylindrically arranged, can fit tightly and ensure that the outer reflector markers attached to the C-arm are visible to a tracking system or the like, while maintaining sterility.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A sterile drape for a trackable medical device having at least one trackable marker spatially trackable by a medical tracking system, comprising
    a draping portion for draping over the trackable medical device;
    a reinforced film portion having a first portion and a second portion, at least the second portion having a viewing surface configured to view therethrough the at least one trackable marker, the reinforced film portion transparent to electromagnetic radiation in at least one of the visible or infrared spectrum, and the reinforced film portion more resistant to folding than the draping portion; and
    a holding or tensing device formed in or on the first portion of the reinforced film portion and operative to draw the reinforced film portion taut or smooth on or over a surface of the medical device to enable the medical tracking system to optically track the at least one trackable marker, wherein said holding or tensing device does not impede transmission of electromagnetic radiation through the viewing surface of the second portion when the electromagnetic radiation emitted or reflected by the at least one trackable marker is normal to the viewing surface,
    wherein the reinforced film portion is shaped so as to maintain a smooth surface.

2. The sterile drape according to claim 1, wherein at least the reinforced film portion is configured as a wrap-around sheath for the medical device.

3. The sterile drape according to claim 1, wherein the reinforced film portion comprises a thickened material that is greater than 1.5 times the thickness of the draping portion.

4. The sterile drape according to claim 1, wherein the reinforced film portion comprises a thickened material that is greater than 3 times the thickness of the draping portion.

5. The sterile drape according to claim 1, wherein the reinforced film portion comprises a thickened material that is greater than 6 times the thickness of the draping portion.

6. The sterile drape according to claim 1, wherein the reinforced film portion comprises a thickened material that is between 1.5 to 15 times the thickness of the draping portion.

7. The sterile drape according to claim 1, wherein the reinforced film portion comprises a thickened material that is between 4 to 12 times the thickness of the draping portion.

8. The sterile drape according to claim 1, wherein the reinforced film portion comprises a thickened material that is between 7 to 10 times the thickness of the draping portion.

9. The sterile drape according to claim 1, wherein the reinforced film portion is configured as a rectangle and extends from one edge of the drape to an opposite edge of the drape.

10. The sterile drape according to claim 1, wherein the holding or tensing device comprises at least one of a belt tie, a belt-hole tie, a rubber tie, a hooked tie or hooked fastening, an adhesive or bonded fastening.

11. The sterile drape according to claim 1, wherein the reinforced film portion is transparent to light in the infrared spectrum.

12. The sterile drape according to claim 1, wherein the portion is hermetically connected to the reinforced film portion, and wherein the reinforced film portion comprises a material different from the draping portion.

13. The sterile drape according to claim 12, wherein a thickness of the reinforced film portion is greater than a thickness of the draping portion.

14. The sterile drape according to claim 12, wherein a thickness of the reinforced film portion is greater than a thickness of the draping portion.

15. A sterile drape for a trackable medical device having at least one trackable marker spatially trackable by a medical tracking system, comprising
  a draping portion for draping over the trackable medical device;
  a reinforced film portion having a first portion and a second portion, at least the second portion having a viewing surface configured to view therethrough the at least one trackable marker, the reinforced film portion transparent to electromagnetic radiation in at least one of the visible or infrared spectrum, and the reinforced film portion more resistant to folding than the draping portion; and
  a holding or tensing device formed in or on the first portion of the reinforced film portion and operative to draw the reinforced film portion taut or smooth on or over a surface of the medical device to enable the medical tracking system to optically track the at least one trackable marker, wherein said holding or tensing device does not impede transmission of electromagnetic radiation through the viewing surface of the second portion when the electromagnetic radiation emitted or reflected by the at least one trackable marker is normal to the viewing surface, wherein the drape is configured as a pouch-like sheath with the reinforced film portion and the drape portion.

16. A sterile drape for a trackable medical device having at least one trackable marker spatially trackable by a medical tracking system, comprising
  a draping portion for draping over the trackable medical device;
  a reinforced film portion having a first portion and a second portion, at least the second portion having a viewing surface configured to view therethrough the at least one trackable marker, the reinforced film portion transparent to electromagnetic radiation in at least one of the visible or infrared spectrum, and the reinforced film portion more resistant to folding than the draping portion; and
  a holding or tensing device formed in or on the first portion of the reinforced film portion and operative to draw the reinforced film portion taut or smooth on or over a surface of the medical device to enable the medical tracking system to optically track the at least one trackable marker, wherein said holding or tensing device does not impede transmission of electromagnetic radiation through the viewing surface of the second portion when the electromagnetic radiation emitted or reflected by the at least one trackable marker is normal to the viewing surface, wherein the reinforced film portion comprises a material different from that of the draping portion.

17. The sterile drape according to claim 16, wherein the reinforced film portion comprises a material that has a higher degree of rigidity relative to the draping portion.

18. A sterile drape for a trackable medical device having at least one trackable marker spatially trackable by a medical tracking system, comprising
  a draping portion for draping over the trackable medical device;
  a reinforced film portion having a first portion and a second portion, at least the second portion having a viewing surface configured to view therethrough the at least one trackable marker, the reinforced film portion transparent to electromagnetic radiation in at least one of the visible or infrared spectrum, and the reinforced film portion more resistant to folding than the draping portion; and
  a holding or tensing device formed in or on the first portion of the reinforced film portion and operative to draw the reinforced film portion taut or smooth on or over a surface of the medical device to enable the medical tracking system to optically track the at least one trackable marker, wherein said holding or tensing device does not impede transmission of electromagnetic radiation through the viewing surface of the second portion when the electromagnetic radiation emitted or reflected by the at least one trackable marker is normal to the viewing surface, wherein the first portion includes a first end and a second end different from the first end, and the holding or tensing device is operative to alter a position of the first end relative to the second end.

19. A sterile drape for a trackable medical device having at least one trackable marker spatially trackable by a medical tracking system, comprising
  a draping portion for draping over the trackable medical device;
  a reinforced film portion having a first portion and a second portion, at least the second portion having a viewing surface configured to view therethrough the at least one trackable marker, the reinforced film portion transparent to electromagnetic radiation in at least one of the visible or infrared spectrum, and the reinforced film portion more resistant to folding than the draping portion; and
  a holding or tensing device formed in or on the first portion of the reinforced film portion and operative to draw the reinforced film portion taut or smooth on or over a surface of the medical device to enable the medical tracking system to optically track the at least one trackable marker, wherein said holding or tensing device does not impede transmission of electromagnetic radiation through the viewing surface of the second portion when the electromagnetic radiation emitted or reflected by the at least one trackable marker is normal to the viewing surface, wherein the holding or tensing device is operative to alter a dimension of the sterile drape.

* * * * *